United States Patent [19]

Jeffries et al.

[11] Patent Number: 5,126,266
[45] Date of Patent: Jun. 30, 1992

[54] XYLOSE-FERMENTING YEAST MUTANTS

[75] Inventors: Thomas W. Jeffries, Madison; Philip L. Livingston, Green Bay, both of Wis.

[73] Assignee: The United States of America as represented by the Secretary of Agriculture, Washington, D.C.

[21] Appl. No.: 188,871

[22] Filed: May 2, 1988

[51] Int. Cl.$^5$ .................. C12P 7/06; C12N 15/01; C12N 1/16

[52] U.S. Cl. .................. 435/255; 435/161; 435/171; 435/172.1; 435/921; 435/938

[58] Field of Search .............. 435/255, 254, 163, 161, 435/172.1, 921, 938

[56] References Cited

U.S. PATENT DOCUMENTS 4,347,317 8/1982 Yoshimura et al. ............... 435/110
4,701,414 10/1987 van Dijken et al. ............... 435/163

OTHER PUBLICATIONS

Jeffries Enz. Microb. Technol. 1984, vol. 6, Jun. (254–258) Mutants of *Pachysolen tannophilus* showing enhanced rates of growth and ethanol formation from D-xylose.

Difco Manual, 9th Edition, Detroit Michigan pp. 47–48 BAGG Broth.

Primary Examiner—Richard A. Schwartz
Assistant Examiner—S. L. Nolan
Attorney, Agent, or Firm—M. Howard Silverstein; John D. Fado

[57] ABSTRACT

A growth medium is provided for mutant mixtures of *Pichia stipitis* or *Candida shehatae* that permits the growth of mutants which are the best xylose-to-ethanol fermenters in the mixture while inhibiting the growth of inefficient fermenters. The medium comprises a mixture of two compounds, the first compound selected from the group consisting of L-xylose, L-arabinose, D-arabinose, glycerol, erythritol, erythrose, 5- and 6-carbon polyols such as xylitol, L-arabinitol, D-arabinitol and mannitol, and wherein the second compound is ammonium tartarate or an inorganic nitrogen source compound such as ammonium chloride or ammonium sulfate.

15 Claims, No Drawings

XYLOSE-FERMENTING YEAST MUTANTS

FIELD

This invention pertains to yeasts which are active as xylose-to-ethanol fermenters. As used herein, unless otherwise indicated, "xylose" refers to the naturally-occurring form, i.e., D-xylose.

PRIOR ART

It is known that xylose, which may be produced from hemicellulose, can be fermented to ethanol by the action of anyone of several yeast species. In the search for better fermenters, typically a single strain is randomly mutagenized, and the resultant mutants are isolated and screened for the best fermenter in the mixture. However, finding the best fermenter is very difficult. That is, without using procedures that identify or favor the growth of mutants, ordinarily it is necessary to examine as many as 100,000–1,000,000 strains to obtain even one that shows enhanced fermentative activity.

An improved method of cultivating mutant mixtures so as to favor the growth of the best xylose-to-ethanol fermenters in the mixture is disclosed in an article by Thomas W. Jeffries in "Enzyme Microbiology Technology", 1984, vol. 6, pp 254–258. In this method, a mutant mixture of *Pachysolen tannophilus* was grown on a medium containing xylitol as a carbon source and nitrate as a nitrogen source. The medium favored the growth of the best xylose-to-ethanol fermenters in the mixture, and inhibited growth of inefficient fermenters. While good results were achieved, the mechanisms were not understood and could not be generalized to other yeast species.

SUMMARY

In the present invention a growth medium for mutant mixtures of *Pichia stipitis* or *Candida shehatae* is provided which favors the growth of the best xylose-to-ethanol fermenters in the mixture while inhibiting growth of inefficient fermenters. The medium includes a carbon source and a nitrogen source, wherein the carbon source is selected from the group consisting of L-xylose, L-arabinose, D-arabinose, glycerol, erythritol, erythrose, 5- and 6-carbon polyols such as xylitol, L-arabinitol, D-arabinitol and mannitol, and wherein the nitrogen source is ammonium tartarate or an inorganic nitrogen source compound such as ammonium chloride or ammonium sulfate.

In selecting the specific carbon and nitrogen sources, it has been discovered that compounds should be employed which do not induce elevated titers of enzymes in the pathway of interest.

To inhibit growth of organisms not capable of rapid fermentation, a respiratory inhibitor may be included in the medium to suppress overall growth of the mutants and force the use of fermentative pathways.

Therefore, an object of the present invention is to employ selective conditions that favor the growth of the better fermentative mutants in the mixture so that the probability of any isolated strain of *P. stipitis* or *C. shehatae* being a better ethanol fermenter for xylose than the parent strain is increased from less than one in a million to greater than one in ten.

A further object is to greatly reduce the amount of labor involved in isolating and screening *P. stipitis* and *C. shehatae* for effective ethanol fermentation agents.

DETAILED DESCRIPTION

In the practice of the present invention, yeast strains of *P. stipitis* or *C. shehatae* are mutated in the prior art manner, e.g., by ultraviolet radiation or nitrosoguanidine. Ultraviolet radiation procedures for yeast strains of this nature are taught by F. Sherman, G. R. Fink and J. B. Hicks, *Methods in Yeast Genetics*, Cold Spring Harbor Laboratory, Cold Spring Harbor, N.Y., 1983.

Procedures for nitrosoguanidine mutation of such strains are taught by R. H. Baltz, "Mutagenesis in Streptomyces spp", in A. L. Demain and N. A. Solomon (editors), *Manual of Industrial Microbiology and Biotechnology*, American Society for Microbiology, Washington, D.C., 1986. In a typical UV metagenesis, the yeast strain is cultivated for about 24 hours on a noninductive medium such as yeast malt extract. Cells are washed from the surface, suspended in distilled water to an optical density of 0.5 at 525 nm (approximately $3 \times 10^7$ cells/ml) and irradiated with 70 $W/cm^{-2}$ for about 12 minutes until a 90–99% kill is obtained.

After mutation, the mutant mixture of cells is combined with the growth medium of the present invention which contains the carbon and nitrogen sources set forth above, and thereafter the broth is treated in the manner of the prior art relating to incubating yeasts.

Typically incubation is carried out in two phases, i.e., an enrichment phase and a plating phase. In the enrichment phase, about 0.1–1.0 ml of mutant mixture generally is combined with about 10 ml of the growth medium.

The carbon source generally is present in the growth medium in an amount of about 5–100 grams, preferably 50 grams per liter of said medium. The nitrogen source generally is present in an amount of about 0.5 to 8 g/L. The amount of nitrogen source employed depends on its nitrogen content. This amount is adjusted so as to provide preferably about 1.0 grams N per L of medium. The other ingredients of the growth medium typically may be mineral salts and vitamins such as present in a yeast nitrogen base medium disclosed in *Difco Manual of Dehydrated Culture Media and Reagents for Microbiological and Clinical Laboratory Procedures*, ninth edition, Difco Laboratories Incorporated, Detroit, Mich., pp 251, 252, except that the medium is free of ammonium sulfate and amino acids.

The broth of mutant mixture and growth medium is held at about 25°–30° C. for about 3 to 10 days. Thereafter, the plating phase of the present invention is carried out wherein enrichment phase broth product, which is a liquid, is plated onto additional growth medium solidified by the addition of agar (typically 1.5%) and having either the same composition as that employed in the enrichment phase or a growth medium which includes alternative carbon- and nitrogen-source materials selected from the compounds disclosed above. In general, about 0.1 to 1.0 ml of enrichment phase broth product is spread onto the surface of the solidified medium, resulting in about $1 \times 10^3$ and $1 \times 10^5$, preferably about $3 \times 10^4$, colony forming units per plate.

The resultant plates are incubated for about 3 to 10 days, preferably about 5 days, at about 25°–30° C., and then refrigerated at 2°–5° C. for up to several more weeks. The faster-growing, more effective xylose-to-ethanol fermenters continue to grow at the lower temperatures and readily can be distinguished after an extended period by inspecting the plates either under a dissecting microscope or with the unaided eye.

To further enhance growth of the more desirable strains while inhibiting growth of the less desirable ones, respiratory inhibitors may be introduced onto the plates when the enrichment phase broth product is plated onto additional growth medium, in order to suppress overall growth and force the use of fermentative pathways. Such inhibitors include antimycin A, salicylhydroxamic acid (SHAM) and sodium azide. Different inhibitors require different optimal concentrations and are best provided at concentrations slightly greater than the lowest necessary to affect growth inhibition in normal cells. In order to achieve these concentrations, the inhibitor preferably first is dissolved in 95% ethanol or water, then dispersed in an aqueous solution of 1.5–2.0% sterile, molten agar.

Ranges and preferred concentrations for the inhibitors in agar are as follows: antimycin A, 0.1–5 mg/ml (1 mg/ml preferred); SHAM, 1–10 mg/ml (4.6 mg/ml preferred); sodium azide, 0.065–1.3 mg/ml (0.65 mg/ml preferred). Agar is poured onto sterile Petri culture dishes and allowed to solidify. Circular plugs of agar (1.0 cm dia.; vol. approximately 0.3 ml) subsequently are cut from the plates and placed on the surface of the freshly innoculated plates of solidified selection medium containing approximately 20 ml of medium.

Some xylose-fermenting yeasts require more than one kind of inhibitor to completely block respiration. In this case, the concentrations of inhibitors, numbers of inhibitors and their distribution on the plate surface can be varied so as to provide single zones of inhibition or multiple overlapping zones of different inhibitors.

In an alternative embodiment, inhibitor(s) can be added directly to the enrichment phase at the time the mutant mixture initially is combined with the growth medium in a preferred amount, per ml of broth, of about 5 micrograms antimycin A, about 25 micrograms SHAM, and about 3 micrograms azide.

After enrichment and plating, the faster-growing strains are isolated and screened for xylose-to-ethanol fermentation activity in the prior art manner. Such isolation and screening procedures are taught in the Jeffries article cited above and in another article by Jeffries in *Biotechnology and Engineering Symposium*, 1982, No. 12, pp 103–110, John Wiley & Sons, Inc. For example, isolation may be carried out by transferring the apparent faster growing strains to a medium containing a small percentage of D-xylose (e.g. 2%), and cultivating for about 24 hours at about 30° C., followed by scraping cells from the plate, suspending same in distilled water to an optical density of about 0.45 at 525 nm, and using an inoculum for a microtube assay.

In a conventional microtube assay, 1.5 ml conical disposable centrifuge tubes with caps that have been pierced using a 22 ga hypodermic needle are employed. Each tube typically contains 0.675 ml of amino acid-free and ammonium sulfate-free medium as disclosed in the Difco Manual set forth above, with 5 to 13.33% D-xylose as a carbon source. Urea (1.13 g/l) and peptone (3.25 g/l) are commonly used as the nitrogen sources. Multiple tubes of broth are inoculated with 0.075 ml of the 24-hour-old cell suspension, inclined at a 45° angle and shaken at 100–150 rpm. At periodic intervals (e.g., every 12 hours) triplicate tubes are removed, centrifuged and the supernatant solutions are assayed for ethanol by automated gas chromatography.

We claim:

1. A method for growing mutagenized yeast produced from a strain of *Pichia stipitis* or *Candida shehatae*, said method favoring the growth of better xylose-to-ethanol fermenters than said strain, while inhibiting the growth of inefficient fermenters, comprising
   combining said mutagenized yeast with a growth medium containing first and second compounds;
   wherein said first compound is selected from the group consisting of L-xylose, L-arabinose, D-arabinose, erythritol, erythrose, L-arabinitol, D-arabinitol, and mannitol;
   wherein said second compound is selected from the group consisting of ammonium tartarate, ammonium sulfate, and ammonium chloride;
   wherein said growth medium provides a carbon source and a nitrogen source for said mutagenized yeast;
   wherein said carbon source consists essentially of said first compound;
   wherein said nitrogen source consists essentially of said second compound;
   maintaining said combination of said mutagenized yeast and growth medium for a period of time sufficient to permit growth of better xylose-to-ethanol fermenters than said strain, while inhibiting growth of inefficient fermenters.

2. The method of claim 1 wherein said first compound is selected from the group consisting of L-xylose, L-arabinose, and D-arabinitol.

3. The method of claim 1 wherein said combination further includes a respiratory inhibitor to force the use of fermentative pathways.

4. The method of claim 3 wherein said respiratory inhibitor is selected from the group consisting of antimycin A, salicylhydroxamic acid and sodium azide.

5. The method of claim 1 wherein said yeast is *P. stipitis*.

6. The method of claim 1 wherein said yeast is *C. shehatae*

7. The method of claim 1 wherein said first compound is L-xylose.

8. The method of claim 1 wherein said second compound is ammonium tartarate.

9. The method of claim 1 wherein said method is carried out in an enrichment phase followed by a plating phase.

10. The method of claim 9 wherein said plating phase further includes the presence of a respiratory inhibitor to force the use of fermentative pathways.

11. The method of claim 10 wherein said respiratory inhibitor is selected from the group consisting of antimycin A, salicylhydroxamic acid and sodium azide.

12. The method of claim 10 wherein said yeast is *P. stipitis*.

13. The method of claim 10 wherein said yeast is *C. shehatae*

14. The method of claim 10 wherein said first compound is L-xylose.

15. The method of claim 10 wherein said second compound is ammonium tartarate.

* * * * *